United States Patent [19]
van der Merwe

[11] Patent Number: 5,423,756
[45] Date of Patent: Jun. 13, 1995

[54] SYRINGE

[76] Inventor: Marius van der Merwe, P.O. Box 1100, Strand, 7140, Cape Province, South Africa

[21] Appl. No.: 59,212

[22] Filed: May 5, 1993

Related U.S. Application Data

[63] Continuation-in-part of Ser. No. 866,974, Apr. 10, 1992, Pat. No. 5,318,537.

[30] Foreign Application Priority Data

Apr. 13, 1991 [GB] United Kingdom ............... 9107910
Jun. 27, 1991 [GB] United Kingdom ............... 9113821

[51] Int. Cl.6 .............................................. A61M 5/00
[52] U.S. Cl. ................... 605/110; 604/218; 604/263
[58] Field of Search .............. 604/110, 218, 228, 192, 604/187, 263, 194, 195

[56] References Cited

U.S. PATENT DOCUMENTS

| | | |
|---|---|---|
| 4,270,536 | 6/1981 | Lemelson . |
| 4,710,170 | 12/1987 | Haber et al. . |
| 4,775,363 | 10/1988 | Sandsdalen . |
| 4,775,364 | 10/1988 | Alles . |
| 4,863,427 | 9/1989 | Cocchi . |
| 4,917,243 | 4/1990 | Abrams . |
| 4,923,443 | 5/1990 | Greenwood et al. . |
| 4,944,397 | 7/1990 | Miller . |
| 4,950,240 | 8/1990 | Greenwood et al. . |
| 4,961,541 | 10/1990 | Hashimoto . |
| 4,965,426 | 10/1990 | Colombo . |
| 5,000,736 | 3/1991 | Kaufhold, Jr. et al. . |

FOREIGN PATENT DOCUMENTS

| | | |
|---|---|---|
| 0278493 | 6/1991 | European Pat. Off. . |
| 2613230 | 4/1991 | France . |
| WO89/08468 | 4/1989 | Japan . |
| 2214082 | 9/1991 | United Kingdom . |
| 2217991 | 10/1991 | United Kingdom . |
| WO90/03197 | 8/1990 | WIPO . |
| WO91/03269 | 6/1991 | WIPO . |
| WO91/08786 | 6/1991 | WIPO . |

Primary Examiner—John D. Yasko
Attorney, Agent, or Firm—Charles D. Gunter, Jr.

[57] ABSTRACT

The present invention provides a needle receiving member adapted to separate a needle from a syringe and to contain the said needle, the needle receiving member being characterized in that it comprises:
a. an axially elongated member having an axially extending needle receiving chamber therein, the member having an axial aperture in a wall thereof through which the needle can be inserted at least in part transversely into the chamber: and in that
b. the needle receiving member incorporates means for separating the needle from a syringe body.

The invention also provides a syringe in which the plunger which drives the piston of the syringe is formed so as to provide the needle receiving member, preferably in part of the plunger shaft which can be separated from the remainder of the plunger shaft by a frangible one use connection so that the syringe can be disabled both by removal of the needle and breaking the plunger mechanism.

13 Claims, 3 Drawing Sheets

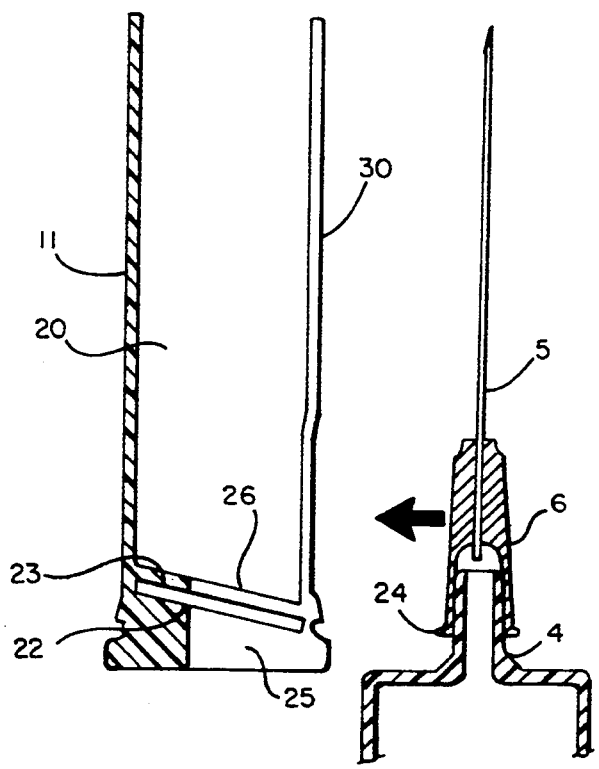
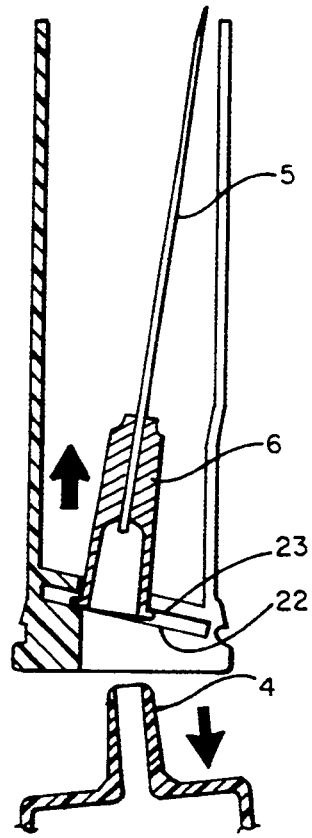
FIG. 5a
FIG. 5b
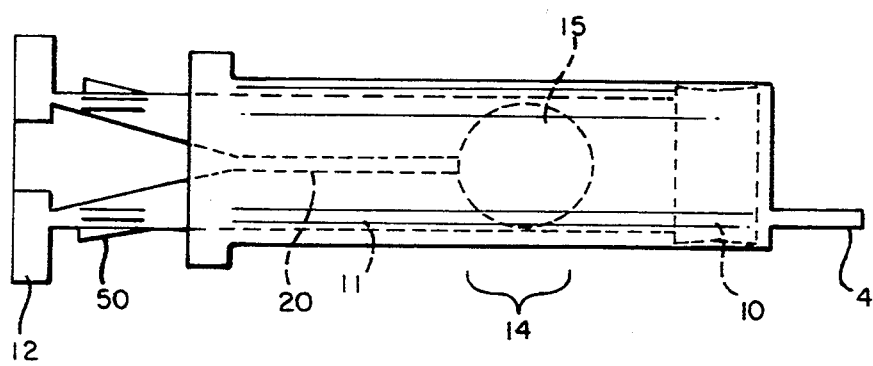
FIG. 6

SYRINGE

This is a continuation-in-part of my application Ser. No. 07/866,974, filed Apr. 10, 1992, now U.S. Pat. No. 5,318,537.

The present invention relates to a syringe, notably to a safety syringe in which the syringe plunger and needle are rendered inoperative after use of the syringe

BACKGROUND TO THE INVENTION

Syringes typically comprise a tubular body having an axial piston bore within which a piston head is moved axially by means of a plunger from a position at or adjacent the proximal end of the piston bore to a position at or adjacent the distal end of the piston bore so as to dispense the contents of the space within the body ahead of the piston via a needle located at or adjacent the distal end of the body which is inserted into or under the skin of a person. Many forms of syringe are known, but they all have these general features and the term syringe will be used hereinafter to denote a dispensing device of this type.

Once a syringe has been used to draw blood or other bodily fluid from a patient or to administer a medicament or other material to a patient, problems arise in the disposal of the used syringe. The syringe can be constructed so that it can be dis-assembled and the individual components cleaned and sterilised for subsequent re-use. However, this is time consuming and costly. It is therefore common practice to dispose of the used syringe to waste, for example into a strong plastic container which is disposed of by incineration or burial. However, in handling the used syringe there is the risk that the handler may accidentally jab himself with the exposed end of the needle prior to or during insertion into the disposal container. Furthermore, the syringe is disposed of in an operative condition so that it can be retrieved from the disposal container for unauthorised re-use, for example to inject illicit drugs or the like.

In order to reduce the risk of accidental jabbing with the used needle, it has been proposed to cut or break the needle off the syringe using a mechanical cutter, such as that described in for example U.S. Pat. Nos. 4,965,426 or 4,961,541, or using a pair of manual cutters with hardened steel blades. However, this will usually leave a sharp stump of the needle exposed which can still injure a user and machines to cut or break the needle are usually expensive and cumbersome and cannot readily be used away from sources of electric power.

It has also been proposed to supply the needle as a separate item enclosed in an axial sheath which must Be removed once the needle has been mounted on the syringe before the syringe can be used. After use the sheath is re-applied axially to the needle to render the needle safe. It has been proposed in GB 2214082 A to incorporate a circumferential rib within the foot of such a sheath which engages with a circumferential groove in the mounting of the needle on the syringe so that the sheath, when pushed fully home on the needle, engages the needle in such a manner that the needle can be separated axially from the syringe when the sheath is withdrawn axially from the syringe. However, such sheaths suffer from the disadvantage that the user must locate the needle tip axially within the narrow bore of the sheath when mounting the sheath upon the needle. There is a risk that the user will stab himself with the tip of the needle in trying to do so.

In a variation of such a sheath it has been proposed, in for example GB 2217991 A, to mount a sheath having an axial slot in the wall thereof terminally upon the syringe. The sheath is pivotally mounted so that in one position it encloses the needle. When the sheath is swung aside, the needle passes transversely through the axial slot and is exposed for use. After use, the sheath is swung back to enclose the needle. However, such sheaths are intended to protect the needle before and after use, they are not intended to remove the needle from the syringe and, due to the nature of their pivot mounting would be incapable of doing so.

Such designs do not affect the operation of the syringe and replacement of the needle can thus render such syringes reusable. It has therefore been proposed, for example in U.S. Pat. No. 4,923,443, to form the plunger with a one use construction so that the plunger can be rendered inoperative once the syringe has been used. Although the syringe is now inoperative, the problems of accidental jabbing with the needle and possible re-use of the needle remain.

In PCT Application WO89/8468 it has been proposed that the plunger should incorporate a frangible section and an axial bore so that after use the plunger can be fully withdrawn and the exposed section of the plunger then broken off at the frangible section. The plunger is thus rendered inoperative and the separated portion can be used as a sheath for the needle which is inserted axially into the axial bore in the plunger. However, such a design requires the axial insertion of the needle into the bore of the plunger with its attendant risk of the user stabbing himself.

In order to minimise the risk of stabbing, it has been proposed, for example in PCT Application WO 91/03269, to provide the needle mounting and the distal end of the plunger with co-operating means whereby the distal end of the plunger engages the needle mounting at the forward end of the plunger stroke and a spring or other means withdraws the needle axially into the hollow centre of the plunger. Such a mechanism is complex and costly to manufacture and still leaves the body of the syringe operative.

The need continues for a simple and effective means for rendering a syringe inoperative and for reducing the risk of accidental injury to the user from the needle.

I have now devised a means by which a syringe can be rendered inoperative at the same time as providing a simple means for disposing of the needle which overcomes the problem of handling and disposing of a sharp object.

SUMMARY OF THE INVENTION

Accordingly, the present invention provides a syringe comprising a body portion having an axial piston bore therein and slideably journalled for axial movement therein a piston member, a plunger adapted to engage the piston member for axial movement of the piston member in the piston bore, and a needle through which the contents of the body portion are to be discharged upon axial movement of the piston member, wherein:

a. the needle is mounted or is adapted to be mounted upon the body of the syringe by a breakable or demountable member whereby the needle can be detached from the syringe body;

b. the syringe is provided with a needle receiving member having an axially extending needle receiving chamber therein, which member has an axial aperture in a wall thereof through which the needle can be inserted at least in part transversely into the chamber: and c. the needle receiving member incorporates means for demounting the needle from the syringe body.

The invention also provides a needle receiving member adapted to separate a needle from a syringe and to contain the said needle, the needle receiving member being characterised in that it comprises:

a. an axially elongated member having an axially extending needle receiving chamber therein, the member having an axial aperture in a wall thereof through which the needle can be inserted at least in part transversely into the said chamber; and in that b. the needle receiving member incorporates means for separating the needle from a syringe body.

Preferably, the plunger of the syringe is one which incorporates a one use connection within the length of the plunger or between the operative (distal) end of the plunger and the piston member. The one use connection can be provided by a member which provides a positive connection on the forward or discharge stroke of the plunger, but Which can be broken or ruptured when the plunger is urged against the forward limit of its travel or is withdrawn, so that the plunger cannot withdraw the piston member axially from the hollow body, thus preventing re-assembly of the plunger and re-use of the syringe after the one use connection is broken or otherwise disabled. It is particularly preferred that the one use connection be a frangible section in the length of the plunger or at the distal end thereof which is either foreshortened axially when the connection is broken and/or is configured so that relative rotation of the remaining portions of the plunger about their common longitudinal axis allows the opposing faces of the broken frangible section to nest within one another whereby the plunger can be foreshortened axially.

I believe that syringes having such a form of plunger are novel and the invention therefore also provides a syringe comprising a body portion having an axial piston bore therein and slideably journalled for axial movement therein a piston member, a plunger adapted to engage the piston member for axial movement of the piston member in the piston bore, the plunger being provided with a one use connection in the length thereof or at or adjacent the distal end thereof whereby the drive between the plunger and the piston member can be disabled, characterised in that the one use connection is a frangible section in the length of the plunger or at the distal end thereof configured so that disabling of the one way connection by breaking the frangible section enables the axial length of the plunger to be decreased. Preferably the frangible section is one which is either foreshortened axially when the connection is broken and/or is configured so that relative rotation of the residual portions of the broken plunger about their common longitudinal axis allows the opposing faces of the broken frangible section to nest within one another whereby the plunger can be foreshortened axially.

It is also preferred that the bore of the cylinder within which the plunger is journalled is provided with one or more inwardly projecting ribs or the like which engage in a corresponding circumferential recess or groove on the plunger. In this way, the axially foreshortened plunger can be inserted into the cylinder and locked within the cylinder by the mutual engagement of the projections and the recesses or groove(s). Preferably, the axial foreshortening of the plunger ensures that the free (proximal) end of the foreshortened plunger is pushed into the bore so as to leave no free end accessible to a user. Such foreshortening of the plunger thus renders the syringe wholly inoperative as well as providing a compact unit for disposal.

It will be appreciated that the projections on the syringe body can be located at the proximal end of the bore or syringe body, so that they engage the proximal end face of the foreshortened plunger rather than a recess formed in the side wall of the plunger. It will also be appreciated that the plunger may carry radially outwardly projecting members which engage a recess or circumferential groove in the wall of the bore. Such projecting members can be sharpened or acutely angled, for example to form sharp teeth or the like, which cut into the wall of the bore to inhibit removal of the plunger once the teeth have engaged to wall of the piston bore. In this case, the projections can be mounted on lever members which are actuated by the user to deploy the projecting members to engage with and cut into the wall when the plunger has been pushed fully home in the piston bore.

In a particularly preferred embodiment, the plunger provides the needle receiving member so that the whole syringe can be broken down after use to demount the needle and house it in the axial chamber within the broken off portion of the plunger via insertion transversely through the axial slot in the wall of the plunger; and the plunger/needle then inserted into the bore of the syringe and pressed fully home therein so that the plunger containing the needle is locked within the cylinder.

Apart from the features of the needle receiving member and the one use connection of the plunger described in greater detail below, the syringe of the invention can be of conventional design and construction. Where the piston plunger provides the needle receiving member as described above, simple replacement of a conventional plunger with a plunger incorporating the needle receiving chamber and, preferably also the frangible one use connection which allows the plunger to be axially foreshortened, enables modification of an existing syringe into a safety syringe having the features of the invention to be achieved.

Accordingly, the present invention also provides a plunger member for use in a syringe, which plunger member comprises:

a. an axially elongated member carrying or adapted to carry a syringe piston member;

b. a one use connection provided in the length of the axially elongated member or at or adjacent the distal end thereof whereby the drive between the plunger and the piston member can be disabled, the one use connection comprising a frangible section configured so that disabling of the one way connection by breaking the frangible section enables the axial length of the plunger to be decreased;

c. an axially extending needle receiving chamber in the axially extending member adapted to receive and retain a needle mounted upon the syringe;

d. an axially extending aperture in a wall of the axially extending member through which aperture the needle can be inserted at least in part transversely into the said chamber; and e. means incorporated in the axially extending member for separating the needle from a syringe body.

Preferably the frangible section is one which is either foreshortened axially when the connection is broken and/or is configured so that relative rotation of the residual portions of the broken plunger about their common longitudinal axis allows the opposing faces of the broken frangible section to nest within one another whereby the plunger can be foreshortened axially.

For convenience, the invention will be described hereinafter in terms of a radially symmetrical syringe having a cylindrical bore within which is journalled a piston for reciprocation by means of a plunger whose proximal end provides a thrust pad or button and whose distal end carries or bears against the piston, and from which fluid is discharged when a user depresses the plunger to eject fluid in the bore of the syringe through an axially orientated needle carried on an axial outlet through the terminal cross wall of the syringe.

The needle can be mounted on the syringe by means of a breakable mounting and the end of the needle receiving member which is to be closest to the syringe during removal of the needle (the proximal end) can be provided with a metal or other strong rim which bears against the mounting as the needle receiving member containing the needle is flexed about the longitudinal axis of the syringe to cause the mounting or the needle to break. It is preferred to incorporate a break line in the plastic moulding which forms the mounting of the needle, for example a circumferential score or thinning in the wall of the mounting, so that the needle can be detached as a whole from the syringe. It may be desirable to provide the needle receiving member with means by which the needle is held firmly within the needle receiving member and axial movement of the needle with respect to the needle receiving member is minimised. The means for holding the needle can, for example, be provided by a tight fit between the needle and at least part of the internal walls of the needle receiving chamber or by a resilient member through which the shank of the needle passes as a tight fit so as to minimise axial movement of the needle within the receiving member during flexing of the needle.

Alternatively, the needle can be demountably mounted on the syringe body, for example by way of a push fit, screw or other mounting which is engaged by the needle receiving member. If desired, the mounting can incorporate a breakable element as described above. Preferably, the mounting is a push fit of a needle support block upon an axial spigot outlet to the syringe body so that the needle as a whole is detached axially from the syringe body.

The needle receiving member is provided by an axially elongated hollow member which has a side, axial needle entry port whereby the user moves the needle transversely with respect to the receiving member when inserting the needle into the receiving means, thus reducing the risk of jabbing himself axially with the needle tip. Where the needle is to be detached by transverse and/or axial movement of the needle mounting with respect to the syringe body, the needle receiving member is provided with suitable separating means located at or adjacent the proximal end of the needle entry port. Thus, where the needle is mounted by means of a screw fit mounting, the needle receiving member incorporates a suitably shaped socket at its proximal end which engages a correspondingly shaped shoulder on the needle mounting so that the mounting can be unscrewed when the needle has been inserted into the needle receiving member. In a preferred embodiment, the mounting of the needle is by way of an axial push fit upon a boss or spigot at the distal end of the syringe body and the mounting is provided with one or more radial projections. These are to be engaged by a ramp or cam-like member at or adjacent the proximal end of the needle receiving member as the needle receiving member moves transversely with respect to the needle mounting. This action moves the needle mounting axially with respect to the syringe so that the needle is separated axially from the syringe.

The radial projections on the needle mounting can be provided by the circumferential shoulder at the proximal end of a conventional mounting block carrying the needle or can be additional projections moulded into the mounting of the needle. It will be appreciated that the radial projections on the needle mounting can be sloped to provided the ramp or camming member and that the projections on the needle receiving member need not then be ramped or cammed. It will also be appreciated that the same action can be achieved by means of an axially inclined groove which is engaged by a rib. For convenience, this form of separation of the needle from the syringe will be described hereinafter in terms of a ramp member carried at or adjacent the proximal end of the needle receiving member engaging with the proximal end shoulder of the needle mounting.

It will be appreciated that the axial needle entry port in the wall of the needle receiving member need not extend the full length of the needle receiving chamber within the needle receiving member, but may be axially shorter than the needle itself so that the user inserts the tip or distal portion of the needle transversely into the axial entry port and then moves the needle axially to complete the insertion of the needle into the needle receiving chamber. However, it is preferred that the entry port extend for at least 50%, preferably from 75 to 100% of the axial length of the needle to be inserted through it, so that insertion of the needle is achieved substantially wholly by a transverse movement between the syringe and the needle receiving member.

The needle receiving chamber is orientated axially within the needle receiving member and extends for the full axial length of the needle it is to receive. However, as indicated above, the needle entry port in a side wall of the chamber need not extend for the full length of the chamber so that a needle once located within the chamber can not readily escape through the entry port.

The chamber can be merely a cylindrical bore within which the needle is a loose fit. However, it is preferred that the needle receiving member incorporate means which positively engage the needle or its mounting so that, once inserted into the chamber, the needle cannot readily be removed. For example, where the needle mounting incorporates a circumferential groove to provide the line of weakness at which the mounting is to break, the proximal end of the chamber can have an internal rib which engages that groove to retain the needle in the chamber once it has been broken away from the syringe. Alternatively or in addition, part of the chamber can be formed as a tight fit upon the needle so that the needle is positively gripped and held within the chamber.

The needle receiving member can be a simple cylindrical member having a blind ended axial bore forming the needle chamber and with the axial entry port formed in one wall thereof. If desired, the distal end of the syringe body and the proximal end of the needle receiving member can have co-operating faces whereby they can pivotally engage one another. The needle receiving member is offered up to the distal end of the syringe and the operating faces mated to one another. The syringe and needle receiving member are then pivoted about the engagement point to bring the needle into engagement with the axial entry port. Due to the shapes of the co-operating faces, registration of the shank of the needle with the port is facilitated. For example, the end face of the syringe body can be formed with a rounded face and the proximal end face of the needle receiving means can carry a corresponding curved portion so that it seats upon the curved face of the syringe and adopts a specific orientation with respect to the syringe when the opposed curved surfaces are correctly engaged. When the syringe and needle receiving means are pivoted with respect to one another, the needle will follow a path defined by the shapes of the opposed faces and can thus be guided accurately into the needle entry port.

The plunger for the syringe preferably incorporates a one use connection with the piston of the syringe so that the plunger and the needle are both disabled after use of the syringe. The piston can be formed integrally with the shaft of the plunger and the one use connection achieved by Weakening the shaft of the plunger at the connection to the piston so that it breaks upon completion of the forward, delivery stroke of the plunger. Alternatively, the one way connection can be disconnected as the plunger is withdrawn from the syringe. Many forms of one way connection may be employed, see for example those described in U.S. Pat. No. 4,923,443. However, the one use connection is one which enables an axial foreshortening of the plunger shaft to be achieved when the residual plunger shaft is re-inserted into the piston bore. Thus, it is preferred that the shaft of the plunger be partially cut away at the one use connection, for example by cutting transverse circular or other shaped portions out of the plunger shaft. When the connection is broken, crenellated, cusped or other co-operating shaped ends to the two opposing ends of the residual parts of the shaft are formed. When one part is rotated relative to the other, the crowns of one part are brought into register with the troughs of the other so that the plunger shaft foreshortens axially.

If desired, the needle can be broken off or detached using a separate needle receiving member which is then discarded or can be inserted into a suitably shaped bore in the plunger body. However, it is particularly preferred that the plunger shaft be formed with an internal bore which accommodates the needle as described above for the needle receiving member, and that this portion of the plunger shaft be withdrawn from the syringe when the one use connection with the piston is broken. In this way, the residue of the plunger shaft can be used to demount and house the needle in the same manner as described above for the needle receiving member. The bore within the plunger shaft can extend from the proximal end of the plunger, ie. that end which the user presses upon to depress the plunger, or can extend from the end face exposed when the one use connection is broken, ie. the distal end.

It is preferred that the proximal end of the plunger be formed with a radially extending shoulder to provide a thrust head upon which a user presses to depress the plunger within the piston bore of the syringe. It is also preferred that this shoulder be provided with a radial slot in register with the axial needle entry port in the wall of the plunger so as to assist location of the needle with the axial entry port.

As indicated above, it is preferred that the syringe body is provided with locking means whereby the broken off proximal portion of the plunger can be pushed fully home into the bore of the syringe due to its axial foreshortening and locked within the bore so that it can not subsequently be removed in an attempt to reconstruct the syringe.

In the preferred embodiment where the plunger shaft acts as the needle receiving member, the syringe is rendered inoperative by destruction of the plunger shaft and removal of the needle, and the inoperative syringe is reduced to an axially foreshortened construction for disposal with the needle safely sheathed within the plunger body.

The syringe of the invention can readily be manufactured by simple modification of the plunger as used in a conventional syringe so as to provide the one use connection and the bore in the plunger to receive the needle. Thus, the syringe body will typically be made from a plastic moulding having the needle extending axially therefrom and secured to the syringe body by a detachable or breakable mounting.

DESCRIPTION OF THE DRAWINGS

To aid understanding of the invention, it will now be described by way of illustration only with respect to preferred forms thereof as shown in the accompanying drawings in which:

FIG. 5A shows in axial cross-section the operation of a preferred form of needle removal mechanism at the proximal end of the needle receiving member;

FIG. 5B shows the continued needle removal operation; and

FIG. 6 shows in diagrammatic axial cross-section an alternative form of the mechanism for locking the foreshortened plunger within the piston bore.

DESCRIPTION OF THE PREFERRED EMBODIMENTS

Figure 1:
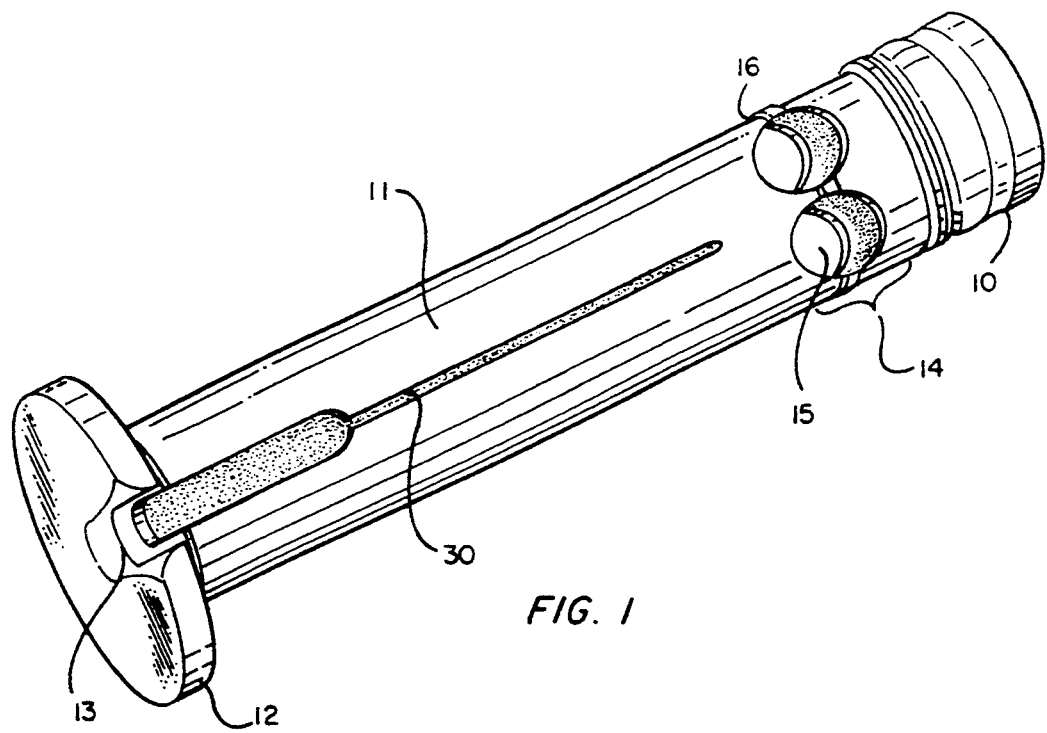
FIG. 1 is a diagrammatic perspective view of the plunger and piston for use in the syringe.
Figure 2:
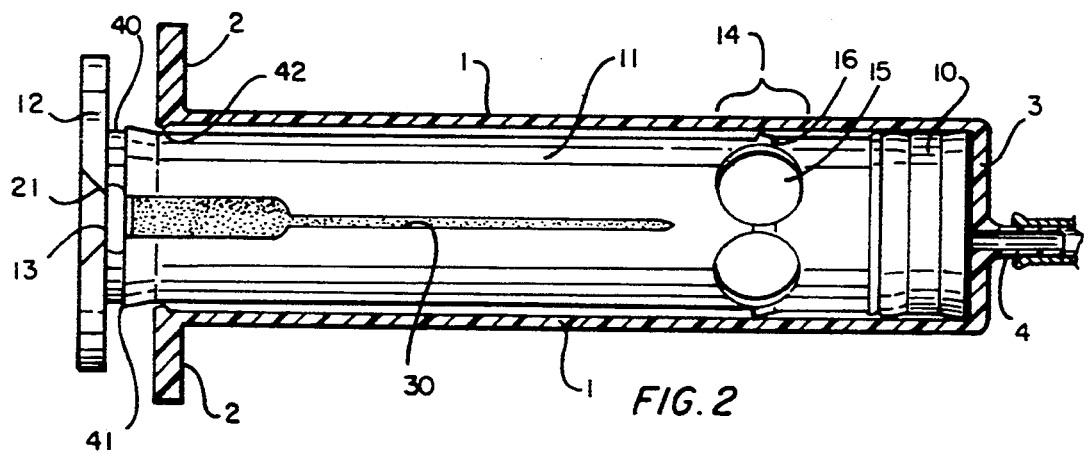
FIG. 2 is an axial cross-sectional view through a syringe incorporating the plunger and piston of FIG. 1 (not shown in section) at the end of the delivery stroke of the piston.
Figure 3:
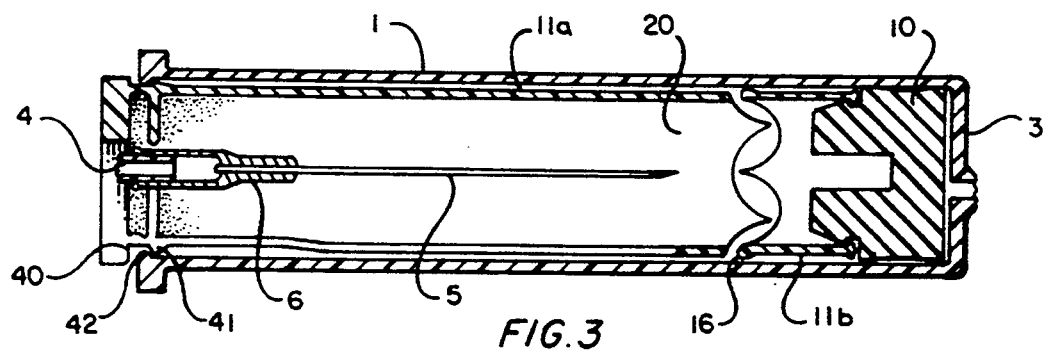
FIG. 3 is an axial cross-sectional view of the syringe and plunger of FIG. 2 in its disabled form, with the needle demounted and housed within the plunger which has been axially foreshortened and re-inserted into the piston bore after use.
Figure 4:
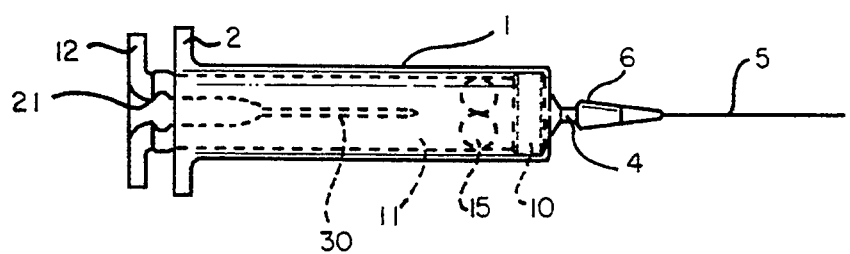
FIG. 4 shows in diagrammatic side views five stages in the operation of the syringe of FIGS. 2 and 3.
Figure 4A:
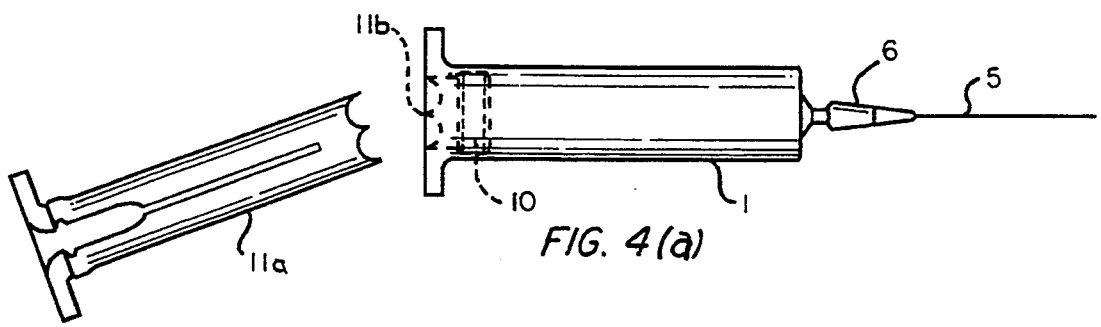
Figure 4B:
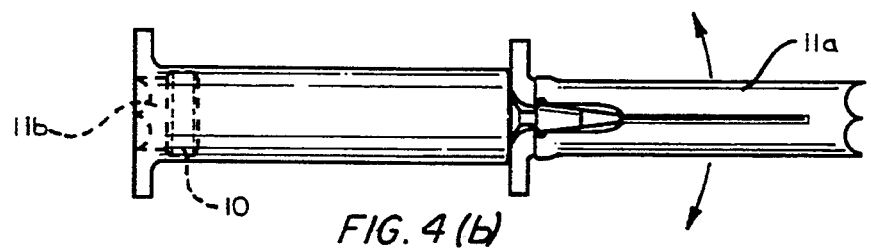
Figure 4C:
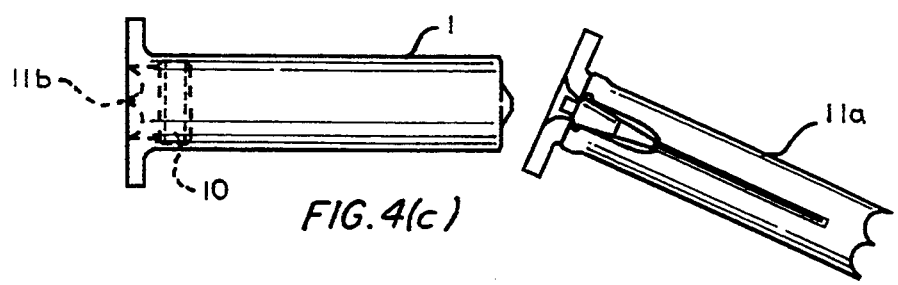
Figure 4D:
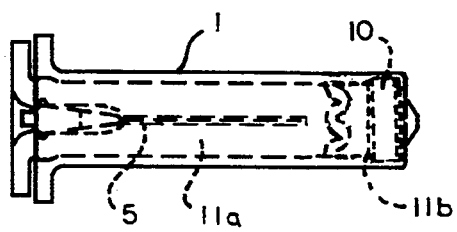

The syringe shown in FIGS. 2, 3 and 4 comprises a generally cylindrical tubular body 1 having a radial shoulder or finger grip projections 2 at the open, proximal, end thereof and an axial piston bore extending from the open end. The other, distal, end of the piston bore is closed by a transverse end wall 3 having an axial outlet spigot 4 upon which is mounted a hypodermic needle 5. As shown in FIG. 5, the needle can be mounted as a push fit upon spigot 4 by means of a needle mounting 6. Alternatively, the needle can be moulded into the spigot 4 during manufacture of the syringe. In this latter case, the spigot 4 or the needle mounting can be formed with a circumferential score or groove to provide a ring of weakness at which the needle 5 can be broken away from the syringe.

Within the piston bore of the syringe body is slideably journalled a piston 10 which is driven axially by a plunger 11 which, in normal use, extends beyond the open end of the syringe body 1 to provide a radially enlarged thrust head 12 against which a user pushes to move the piston axially within the piston bore.

The plunger shaft preferably also acts as the receptacle for the needle 5 when it is detached from the syringe body. Thus, the plunger shaft 11 has an axial bore 20 therein which is adapted to act as the needle receiving chamber. The plunger shaft 11 can be solid with the bore 20 formed axially therein, but is preferably hollow as shown with an axial needle entry port 30 in the side wall thereof which communicates with the central axial bore 20. The entry port 30 feeds the needle radially into the axial bore 20 within the shaft 11 and the radially outward lips of the entry port can be belled to assist location of the needle into the port 30. The bore 20 can extend axially from the distal or proximal end faces of plunger shaft 11 and the radially projecting thrust head 12 can have a radial slot 13 formed therein in register with the proximal end of port 30 to aid correct location of the needle 5 with respect to the entry port 30 when the plunger is used to remove and house the needle 5 as described below.

Where the needle 5 is to be separated from the syringe by snapping the needle mounting 5 or spigot 4 at the line of weakness introduced by the circumferential groove in the needle mounting, as shown in steps 3 and 4 of FIG. 4, it is preferred to form the bore 20 as a close fit upon the needle 5 so that the needle is held firmly within the bore. It is also preferred to form the proximal end of the bore with a sharp rim or lip 21 about which the mounting or spigot flexes so as to assist breaking of the mounting or spigot at the desired point.

Where the needle 5 is mounted as a push fit upon the spigot 4 and is to be lifted off the spigot as the needle receptacle is moved transversely, the proximal end of the plunger bore 20 is provided with at least one transverse ramp member 22 as shown in FIG. 5. Preferably, a second ramp member 23 is provided axially further into the bore 20 to trap the circumferential bead 24, usually present at the proximal end of a conventional needle mounting 6, between the opposed faces of the two ramps 22 and 23. The two ramps are each cut with a radial slot 25 and 26 which are a close fit upon the axial portions of the spigot 4 and the needle mounting 6 respectively so that the upper, distal, face of the proximal ramp 22 bears against the underside, proximal face, of the mounting 6 and the distal ramp 23 guides and retains the mounting 6. As shown in FIG. 5, progressive transverse engagement of the syringe and needle with the ramps 22 and 23 as the needle 5 is inserted transversely into the axial port 30 lifts the needle 5 and its mounting 6 axially off the spigot 4 to detach the needle from the syringe. The angle of the ramps 22 and 23 can be selected in known manner from a knowledge of the geometry of the spigot and the mounting 6 to achieve the required extent of axial movement to separate the needle from the syringe.

It is preferred that the proximal end of the plunger shaft 11 carry an external circumferential groove 40 or a circumferential rib 41 which will engage with a circumferential rib 42 at the lip of the open end of the piston bore to retain the foreshortened piston shaft within the piston bore as described below.

In the above forms of the syringe, the needle 5 is retained in the chamber 20 within the plunger shaft 11.

However, the chamber 20 can be provided by a separate component which has the features described above for removing the needle from the syringe and retaining it captive within the needle chamber 20.

Where the plunger 11 is to provide the needle receiving means as described above, it is preferred that the shaft of the plunger be formed so that the shaft can be broken to disable the plunger. This also allows at least part of the plunger to be removed from the piston bore and presented to the needle so that the needle can be inserted into the chamber 20 within the shaft of the plunger via the entry port 30. The shaft and needle are then preferably re-inserted into the piston bore in the syringe body with the shaft of the plunger axially foreshortened, the engagement of the groove 40 with, and/or the snap passage of rib 41 past, rib 42 serving to retain the foreshortened plunger within the piston bore to inhibit any attempt to re-assemble the syringe for subsequent re-use.

Thus, the plunger 11 is preferably provided at or adjacent the piston 10, ie. at its distal end, with a one time use connection 14. This can be a frangible connection which is broken when the piston butts against the end wall 3 and pressure is applied to the connection as the user attempts to depress thrust head 12 further. However, a particularly preferred form of one use connection is provided by means of a series of radial bores, apertures or cut outs 15 through the plunger shaft 11 adjacent the piston 10, which remove a substantial portion of the material of the shaft at this point. This forms a weak point at which the shaft 11 can be broken by flexing the shaft. Where the plunger shaft is solid, the piston end of the plunger shaft can be formed with an axial recess so that the wall thickness of the shaft is reduced at this end, and the transverse bores or cut outs 15 are formed in this thinner wall area of the shaft.

The cut outs 15 are configured so that they will allow the broken ends of the plunger shaft to nest upon one another and thus achieve a degree of axial foreshortening of the plunger shaft. Thus, the cut outs can be circular or ovals, triangles, rectangles or other axially elongated shapes which provide a narrow remainder to the plunger wall between adjacent cut outs. When the plunger shaft is broken, the break will occur at these narrow remainders to give a crenellated end to each of the sections 11a and 11b of the plunger shaft. The crenellations on one end can be moved out of register with those on the other end by relative rotation of the two ends about the longitudinal axis of the plunger sections so that the raised portions or crowns of one crenellated end will nest in the troughs of the other crenellated end to achieve the axial foreshortening of the plunger shaft.

Preferably, the plunger shaft 11 is provided with one or more radial projections 16 on the shaft portion 11b which is located distally of the one use connection 14. These are to engage the radial rib 42 described above to prevent the whole of the plunger being withdrawn from the piston bore. The engagement of the ribs 42 and 16 also serves to locate the weak point in the shaft approximately in register with the rim of the open end of the piston bore which can then act as the fulcrum about which the plunger shaft is flexed to break the shaft.

For use, the syringe is assembled by mounting the needle 5 upon the syringe body and inserting the plunger 11 and piston 10 into the piston bore in the syringe body—step 1 in FIG. 4. Apart from the cut outs 14, the bore 20 and the axial needle entry port 30 in the plunger shaft 11, the needle, its mounting and the remainder of the syringe can be of conventional design and construction.

In use, the piston 11 is withdrawn in the piston bore to suck medicament or other fluid into the piston bore in the conventional manner. The fluid is injected in the conventional manner by depressing the thrust head 12 to drive the piston 10 axially. After use, the plunger shaft 11 is withdrawn until the projections 16 on the shaft 11 engage the rib 42 at the lip of the piston bore. The shaft is then flexed laterally to cause it to break at the ring of weakness introduced by the cut outs 14—step 2 in FIG. 4.

The proximal section 11a of the shaft 11 is then applied transversely to the needle end of the syringe so that the needle 5 is inserted transversely into the bore 20—step 3 in FIG. 4.

Where the needle is to be broken off the syringe body, the plunger section 11a is flexed as shown in step 3 of FIG. 4 about the longitudinal axis of the needle to break the spigot 4 or the needle mounting 6 as shown in step 4 of FIG. 4 to leave the needle 5 and the residue of the mounting or spigot held in the bore 20 of the shaft section as shown in FIG. 3.

With the alternative form of construction shown in FIG. 5, the ramp 23 engages the underside of the needle mounting 6 and moves the mounting 6 axially with respect to the spigot 4 as the needle is inserted transversely into the axial slot 30. Where the second ramp 23 is present, this can trap the mounting against the upper face of ramp 22 and thus retain the needle and its mounting securely within the bore 20.

The shaft section 11a carrying needle 5 in bore 20 is then reinserted into the piston bore of the syringe body 1. By aligning the crenellated ends of the two sections 11a and 11b relative to one another as described above, the axially projecting portions are out of alignment with one another, and the axial length of the plunger shaft 11 can be reduced to allow the plunger to be inserted far enough axially into the piston bore to allow rib 42 at the lip of the piston bore to engage in the groove 40 in the plunger shaft and thus lock the shaft within the piston bore—step 5 in FIG. 4 and as shown in FIG. 3.

In the alternative form of construction shown in FIG. 6, the proximal end of the plunger is formed with two or more sharp radial teeth 50. When the remnant 11a of the plunger shaft carrying the needle in the axial bore 20 is inserted into the piston bore, lateral pressure on the thrust head 12 flexes the end of the plunger shaft and allows teeth 50 to retract radially and thus fit into the proximal end of the piston bore. When the lateral pressure is released, the end of the plunger shaft expands radially causing the teeth 50 to bite into the wall of the piston bore and thus lock the plunger shaft within the bore. Alternatively, the teeth 50 may not be retracted and the plunger forced axially into the piston bore to engage the teeth 50 with the inner face of the piston bore.

Using the features of the invention, the syringe provides its own needle breaker and receptacle means, which aids the safe disposal of the needle and syringe, as well as rendering the syringe inoperative by breaking the plunger shaft.

I claim:

1. A syringe comprising a body portion having an axial piston bore therein and journalled for axial movement therein a piston member, a plunger adapted to engage the piston member for axial movement of the piston member in the piston bore, said body portion carrying or being adapted to carry a needle through which the contents of the body portion are to be discharged upon axial movement of the piston member; wherein:
   a. the needle is mounted or is adapted to be mounted upon the body of the syringe by a breakable or demountable member whereby the needle can be detached from the syringe body;
   b. the syringe is provided with a needle receiving member having an axially extending needle receiving chamber therein, the needle receiving member having an axial aperture in a wall thereof through which the needle can be inserted at least in part transversely into the chamber;
   c. the needle receiving member incorporates means for separating the needle from the syringe body;
   wherein the plunger of the syringe is one which incorporates a one use connection within the length of the plunger or between the operative, distal end of the plunger and the piston member; and
   wherein the one use connection is a frangible section in the length of the plunger or at the distal end thereof which is either foreshortened axially when the connection is broken and/or is configured so that relative rotation of the remaining portions of the plunger about their common longitudinal axis allows the opposing faces of the broken frangible section to nest within one another whereby the plunger can be foreshortened axially.

2. A syringe comprising a body portion having an axial piston bore therein and journalled for axial movement therein a piston member, a plunger adapted to engage the piston member for axial movement of the piston member in the piston bore, said body portion carrying or being adapted to carry a needle through which the contents of the body portion are to be discharged upon axial movement of the piston member; wherein:
   the needle is mounted or is adapted to be mounted upon the body of the syringe by a breakable or demountable member whereby the needle can be detached from the syringe body;
   the syringe is provided with a needle receiving member having an axially extending needle receiving chamber therein, the needle receiving member having an axial aperture in a wall thereof through which the needle can be inserted at least in part transversely into the chamber;
   the needle receiving member incorporates means for separating the needle from the syringe body; and
   wherein the plunger for use with the syringe comprises:
   a. an axially elongated member carrying or adapted to carry the syringe piston member;
   b. a one use connection provided in the length of the axially elongated member or at or adjacent the distal end thereof whereby the drive between the plunger and the piston member can be disabled, the one use connection comprising a frangible section configured so that disabling of the one way connection by breaking the frangible section enables the axial length of the plunger to be decreased;
   c. an axially extending needle receiving chamber in the axially extending member providing a needle receiving member adapted to receive and retain a needle mounted upon the syringe;
   d. an axially extending aperture in a wall of the axially extending member through which aperture the needle can be inserted at least in part transversely into the said chamber; and e. means incorporated in the axially extending member for separating the needle from a syringe body.

3. A syringe as claimed in claim 2, wherein the needle is mounted or is adapted to be mounted on the syringe body by means of a detachable mounting, and the needle receiving member incorporates means for moving the needle axially with respect to the syringe body as the needle is inserted transversely into the needle receiving member so as to separate the needle from the syringe body.

4. A syringe as claimed in claim 3, wherein the needle mounting is provided with one or more radial projections or recesses adapted to engage with one or more ramp members on the needle receiving member or vice versa so that the needle is moved axially off the syringe body when the needle is introduced transversely into the needle receiving means.

5. A syringe as claimed in claim 4, wherein locking means are provided between the plunger and the syringe body whereby the plunger shaft carrying the needle in the axial bore thereof can be retained within the piston bore.

6. A syringe comprising a body portion having an axial piston bore therein and journalled for axial movement therein a piston member, an axially extending plunger member adapted to engage the piston member for axial movement of the piston member in the piston bore, said body portion carrying or being adapted to carry a needle through which the contents of the body portion are to be discharged upon axial movement of the piston member; wherein:

a. the needle is mounted or is adapted to be mounted upon the body of the syringe by a breakable or demountable member whereby the needle can be detached externally from the syringe body;

b. the plunger member incorporates an axially extending needle receiving chamber adapted to receive and retain a needle mounted upon the syringe;

c. an aperture in a wall of the axially extending plunger member extending axially for at least the length of the needle whereby the needle can be inserted transversely through the aperture into the said chamber;

d. the plunger member incorporates a one use connection within the length of the plunger or between the operative, distal end of the plunger and the piston member whereby the drive between the piston member and the plunger member can be disabled by disconnection of the one use connection; and e. the plunger member incorporates means for separating the needle from the syringe body.

7. A syringe as claimed in claim 6, wherein the one use connection is provided by a member which provides a positive connection on the forward or discharge stroke of the plunger member, but which can be broken or ruptured when the plunger member is urged against the forward limit of its travel or is withdrawn.

8. A syringe as claimed in claim 6, wherein the one use connection is a frangible section in the length of the plunger member or at the distal end thereof which is either foreshortened axially when the connection is broken and/or is configured so that relative rotation of the remaining portions of the plunger member about their common longitudinal axis allows the opposing faces of the broken frangible section to nest within one another whereby the plunger member can be foreshortened axially.

9. A plunger member suitable for use in a syringe as claimed in claim 6, which plunger member comprises:

a. an axially elongated member carrying or adapted to carry a syringe piston member;

b. a one use connection provided in the length of the axially elongated member or at or adjacent the distal end thereof whereby the drive between the plunger member and the piston member can be disabled, the one use connection comprising a frangible section configured so that disabling of the one way connection by breaking the frangible section enables the axial length of the plunger member to be decreased;

c. an axially extending needle receiving chamber in the axially extending member adapted to receive and retain a needle mounted upon the syringe;

d. an axially extending aperture in a wall of the axially extending member, through which aperture the needle can be inserted at least in part transversely into the said chamber; and e. means incorporated in the axially extending member for separating the needle from a syringe body.

10. A syringe as claimed in claim 6 or a plunger as claimed in claim 9, wherein the needle is mounted or is adapted to be mounted on the syringe body by means of a detachable mounting, and the plunger member incorporates means for moving the needle axially with respect to the syringe body as the needle is inserted transversely into the needle receiving chamber so as to separate the needle from the syringe body.

11. A syringe or plunger as claimed in claim 10, wherein the needle mounting is provided with one or more radial projections or recesses adapted to engage with one or more ramp members carried by the plunger member or vice versa so that the needle is moved axially off the syringe body when the needle is introduced transversely into the needle receiving chamber.

12. A syringe as claimed in claim 6, wherein the plunger member has an axial chamber which is to receive the needle and a side wall of the plunger member has an axial aperture through which the needle can be inserted transversely into the axial chamber, the one use connection being provided intermediate the piston member and the axial chamber whereby that part of the plunger member provided with the axial chamber can be separated from the body of the syringe upon disconnection of the one use connection, the needle inserted transversely into the axial chamber in the plunger member via the axial aperture, and the plunger member containing the needle re-inserted into the piston bore.

13. A syringe as claimed in claim 12, wherein locking means are provided between the plunger member and the syringe body whereby the plunger member carrying the needle in the axial needle receiving chamber thereof can be retained within the piston bore.

* * * * *